US008760655B2

(12) United States Patent
Hayashi et al.

(10) Patent No.: US 8,760,655 B2
(45) Date of Patent: Jun. 24, 2014

(54) DIE INSPECTION METHOD

(75) Inventors: Hidekazu Hayashi, Osaka (JP); Takao Imaoku, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 29 days.

(21) Appl. No.: 13/698,395

(22) PCT Filed: May 17, 2011

(86) PCT No.: PCT/JP2011/061337
§ 371 (c)(1),
(2), (4) Date: Nov. 16, 2012

(87) PCT Pub. No.: WO2011/145625
PCT Pub. Date: Nov. 24, 2011

(65) Prior Publication Data
US 2013/0063725 A1 Mar. 14, 2013

(30) Foreign Application Priority Data
May 19, 2010 (JP) ................................. 2010-115733

(51) Int. Cl.
*G01J 3/52* (2006.01)
*G01B 11/28* (2006.01)
*G01R 35/00* (2006.01)
*G01J 3/46* (2006.01)
*G01B 11/06* (2006.01)
*G01B 21/08* (2006.01)

(52) U.S. Cl.
CPC .. *G01J 3/46* (2013.01); *G01J 3/465* (2013.01);
*G01B 11/06* (2013.01); *G01B 11/0616*
(2013.01); *G01B 11/0625* (2013.01); *G01B 11/0633* (2013.01); *G01B 21/08* (2013.01)
USPC ........... 356/405; 356/421; 356/422; 356/423; 356/424; 356/630; 702/91

(58) Field of Classification Search
CPC ............ G01J 3/46; G01J 3/465; G01B 11/06; G01B 11/0616; G01B 11/0625; G01B 11/0633; G01B 21/08
USPC .............................. 356/402–425, 630; 702/91
See application file for complete search history.

(56) References Cited

U.S. PATENT DOCUMENTS 6,359,735 B1    3/2002  Gombert et al.
7,365,860 B2*   4/2008  Price .............................. 356/503

(Continued)

FOREIGN PATENT DOCUMENTS

JP    2001517319 A    10/2001
JP    2003531962 A    10/2003

(Continued)

OTHER PUBLICATIONS

International Search Report.

(Continued)

*Primary Examiner* — Tarifur Chowdhury
*Assistant Examiner* — Sunghee Y Gray
(74) *Attorney, Agent, or Firm* — Harness, Dickey & Pierce, P.L.C.

(57) ABSTRACT

A method is disclosed for inspecting a mold which has a porous alumina layer over its surface. The method includes providing, based on a relationship between a first parameter indicative of a thickness of the porous alumina layer and a color parameter indicative of a color of reflected light from the porous alumina layer, first color information which represents a tolerance of the first parameter of a porous alumina layer which has an uneven structure that is within a tolerance; providing a mold which is an inspection subject, the mold having a porous alumina layer over its surface; obtaining a color parameter which is indicative of a color of reflected light from the porous alumina layer of the inspection subject mold; and determining a suitability of the first parameter of the inspection subject mold based on the obtained color parameter and the first color information.

7 Claims, 8 Drawing Sheets

(56) References Cited

U.S. PATENT DOCUMENTS

| | | | |
|---|---|---|---|
| 8,184,303 B2* | 5/2012 | Sakai et al. | 356/630 |
| 2003/0205475 A1 | 11/2003 | Sawitowski | |
| 2007/0062447 A1* | 3/2007 | Hayashi et al. | 118/713 |
| 2007/0159698 A1 | 7/2007 | Taguchi et al. | |

FOREIGN PATENT DOCUMENTS

| | | | | |
|---|---|---|---|---|
| JP | 2005156695 A | 6/2005 | | |
| JP | 2005171306 A | 6/2005 | | |
| JP | 2005200679 A | 7/2005 | | |
| JP | 2005283556 A | 10/2005 | | |
| JP | 2007024869 A | 2/2007 | | |
| JP | WO2008011471 | * | 9/2008 | G01B 11/06 |
| JP | 2010100941 A | 5/2010 | | |
| WO | WO-0183198 A1 | 11/2001 | | |
| WO | WO-2005085806 A1 | 9/2005 | | |
| WO | WO-2006059686 A1 | 6/2006 | | |
| WO | WO-2006135097 A1 | 12/2006 | | |

OTHER PUBLICATIONS

International Preliminary Report on Patentability dated Dec. 20, 2012.

* cited by examiner (a)

(b)

(a) 3min
(b) 5min
(c) 10min
(d) 15min

DIE INSPECTION METHOD

TECHNICAL FIELD

The present invention relates to a mold inspection method. In this specification, the "mold" includes molds that are for use in various processing methods (stamping and casting), and is sometimes referred to as a stamper. The "mold" can also be used for printing (including nanoimprinting).

BACKGROUND ART

Display devices for use in TVs, cell phones, etc., and optical elements, such as camera lenses, etc., usually adopt an antireflection technique in order to reduce the surface reflection and increase the amount of light transmitted therethrough. This is because, when light is transmitted through the interface between media of different refractive indices, e.g., when light is incident on the interface between air and glass, the amount of transmitted light decreases due to, for example, Fresnel reflection, thus deteriorating the visibility.

An antireflection technique which has been receiving attention in recent years is forming over a substrate surface a very small uneven pattern in which the interval of recessed portions or raised portions is not more than the wavelength of visible light ($\lambda$=380 nm to 780 nm). See Patent Documents 1 to 4. The two-dimensional size of a raised portion of an uneven pattern which performs an antireflection function is not less than 10 nm and less than 500 nm.

This method utilizes the principles of a so-called moth-eye structure. The refractive index for light that is incident on the substrate is continuously changed along the depth direction of the recessed portions or raised portions, from the refractive index of a medium on which the light is incident to the refractive index of the substrate, whereby reflection of a wavelength band that is subject to antireflection is prevented.

The moth-eye structure is advantageous in that it is capable of performing an antireflection function with small incident angle dependence over a wide wavelength band, as well as that it is applicable to a number of materials, and that an uneven pattern can be directly formed in a substrate. As such, a high-performance antireflection film (or antireflection surface) can be provided at a low cost.

As the method of forming a moth-eye structure, using an anodized porous alumina layer which is obtained by means of anodization of aluminum has been receiving attention (Patent Documents 2 to 4).

Now, the anodized porous alumina layer which is obtained by means of anodization of aluminum is briefly described. Conventionally, a method of forming a porous structure by means of anodization has been receiving attention as a simple method for making nanometer-scale micropores (very small recessed portions) in the shape of a circular column in a regular arrangement. An aluminum base is immersed in an acidic electrolytic solution of sulfuric acid, oxalic acid, phosphoric acid, or the like, or an alkaline electrolytic solution, and this is used as an anode in application of a voltage, which causes oxidation and dissolution. The oxidation and the dissolution concurrently advance over a surface of the aluminum base to form an oxide film which has micropores over its surface. The micropores, which are in the shape of a circular column, are oriented vertical to the oxide film and exhibit a self-organized regularity under certain conditions (voltage, electrolyte type, temperature, etc.). Thus, this anodized porous alumina layer is expected to be applied to a wide variety of functional materials.

A porous alumina layer formed under specific conditions includes cells in the shape of a generally regular hexagon which are in a closest packed two-dimensional arrangement when seen in a direction perpendicular to the film surface. Each of the cells has a micropore at its center. The arrangement of the micropores is periodic. The cells are formed as a result of local dissolution and growth of a coating. The dissolution and growth of the coating concurrently advance at the bottom of the micropores which is referred to as a barrier layer. As known, the size of the cells, i.e., the interval between adjacent micropores (the distance between the centers), is approximately twice the thickness of the barrier layer, and is approximately proportional to the voltage that is applied during the anodization. It is also known that the diameter of the micropores depends on the type, concentration, temperature, etc., of the electrolytic solution but is, usually, about ⅓ of the size of the cells (the length of the longest diagonal of the cell when seen in a direction vertical to the film surface). Such micropores of the porous alumina may constitute an arrangement which has a high regularity (periodicity) under specific conditions, an arrangement with a regularity degraded to some extent depending on the conditions, or an irregular (non-periodic) arrangement.

Patent Document 2 discloses a method of producing an antireflection film (antireflection surface) with the use of a stamper which has an anodized porous alumina film over its surface.

Patent Document 3 discloses the technique of forming tapered recesses with continuously changing pore diameters by repeating anodization of aluminum and a pore diameter increasing process.

The applicant of the present application discloses, in Patent Document 4, the technique of forming an antireflection film with the use of an alumina layer in which very small recessed portions have stepped lateral surfaces.

As described in Patent Documents 1, 2, and 4, by providing an uneven structure (macro structure) which is greater than a moth-eye structure (micro structure) in addition to the moth-eye structure, the antireflection film (antireflection surface) can be provided with an antiglare function. The two-dimensional size of a raised portion of the uneven structure which is capable of performing the antiglare function is not less than 1 μm and less than 100 μm. The entire disclosures of Patent Documents 1, 2, and 4 are herein incorporated by reference.

Utilizing an anodized porous aluminum film can facilitate the manufacture of a mold which is used for formation of a moth-eye structure over a surface (hereinafter, "moth-eye mold"). In particular, as described in Patent Documents 2 and 4, when the surface of the anodized aluminum film as formed is used as a mold without any modification, a large effect of reducing the manufacturing cost is achieved. The structure of the surface of a moth-eye mold which is capable of forming a moth-eye structure is herein referred to as "inverted moth-eye structure".

A known antireflection film production method with the use of a moth-eye mold uses a photocurable resin. Firstly, a photocurable resin is applied over a substrate. Then, an uneven surface of a moth-eye mold which has undergone a mold release treatment is pressed against the photocurable resin in vacuum. Thereafter, the uneven structure is filled with the photocurable resin. Then, the photocurable resin in the uneven structure is irradiated with ultraviolet light so that the photocurable resin is cured. Thereafter, the moth-eye mold is separated from the substrate, whereby a cured layer of the photocurable resin to which the uneven structure of the moth-eye mold has been transferred is formed over the surface of the substrate. The method of producing an antireflection film with the use of the photocurable resin is disclosed in, for example, Patent Document 4.

To enable stable mass-production of an antireflection film with the use of a surface of an anodized porous alumina film as a mold without making any modification, it is necessary to manage whether or not the uneven structure at the surface of the anodized porous alumina layer has a predetermined structure. Specifically, it is necessary to check that a surface of a manufactured mold has a desired uneven structure and that the uneven structure at the surface of the mold is not out of a desired range due to wear or damage in the process of mass-production of an antireflection film.

CITATION LIST

Patent Literature

Patent Document 1: Japanese PCT National Phase Laid-Open Publication No. 2001-517319
Patent Document 2: Japanese PCT National Phase Laid-Open Publication No. 2003-531962
Patent Document 3: Japanese Laid-Open Patent Publication No. 2005-156695
Patent Document 4: WO 2006/059686

SUMMARY OF INVENTION

Technical Problem

The uneven structure at the surface of a moth-eye mold is a minute structure of less than 1 µm. To evaluate the size and shape of the uneven structure somewhat quantitatively, it is necessary to use a SEM (scanning electron microscope), for example. From a SEM image of the surface, the distance between adjacent recessed portions ($D_{int}$) and the two-dimensional size of recessed portions ($D_p$) are determined. From a SEM image of a cross-section, the depth of recessed portions ($D_{depth}$) and the thickness of a porous alumina layer ($t_p$) are determined. However, to obtain SEM images, it is necessary to partially destroy the moth-eye mold, and moreover, there is a problem that it requires time. Further, to determine the quality of a mold based on SEM images, it is necessary to convert the above parameters obtained from the SEM images into numerical expressions.

The present invention was conceived for the purpose of solving the above problems. One of the major objects of the present invention is to provide a method for nondestructively and readily inspecting, in the step of forming a surface which has a minute uneven structure whose $D_p$ is less than 1 µm, such as a surface of a moth-eye mold, whether or not the minute uneven structure at the surface is within a predetermined range.

Solution to Problem

A mold inspection method of the present invention is a method for inspecting a mold which has a porous alumina layer over its surface, the porous alumina layer having a plurality of minute recessed portions, the method including the steps of: (a) providing, based on a relationship between a first parameter that is indicative of a thickness of the porous alumina layer and a color parameter that is indicative of a color of reflected light from the porous alumina layer, first color information which represents a tolerance of the first parameter of a porous alumina layer which has an uneven structure that is within a tolerance; (b) providing a mold which is an inspection subject, the mold having a porous alumina layer over its surface; (c) obtaining a color parameter which is indicative of a color of reflected light from the porous alumina layer of the inspection subject mold; and (d) determining a suitability of the first parameter of the inspection subject mold based on the obtained color parameter and the first color information.

In one embodiment, the color parameter includes X or Y of tristimulus values X, Y and Z.

In one embodiment, step (a) includes expressing the relationship of the first parameter and X or Y as an approximation formula.

In one embodiment, step (c) includes measuring a spectral reflectance of the porous alumina layer of the inspection subject mold.

In one embodiment, step (c) includes obtaining the color parameter from each of a plurality of different positions over a surface of the porous alumina layer, and step (d) includes determining a suitability of the first parameter of the inspection subject mold based on the color parameter obtained from each of the plurality of different positions and the first color information.

In one embodiment, the mold inspection method further includes the step of: (e) determining a suitability of the first parameter of the inspection subject mold based on a relationship between a position over a surface of the porous alumina layer and the first parameter.

In one embodiment, the mold inspection method further includes the steps of: (f) providing, based on a relationship between a second parameter that is indicative of an occupancy of the plurality of minute recessed portions of the porous alumina layer and a color parameter that is indicative of a color of reflected light from the porous alumina layer, second color information which represents a tolerance of the second parameter of a porous alumina layer which has an uneven structure that is within a tolerance; and (g) determining a validity of the second parameter of the inspection subject mold based on the obtained color parameter and the second color information.

Step (a) and step (d) may be replaced by step (f) and step (g). In this case, the second color information provided in step (f) includes X or Y of the tristimulus values X, Y and Z, and the color parameter obtained in step (c) includes X or Y of the tristimulus values X, Y and Z. Step (f) includes the step of expressing the relationship between the second parameter and X or Y as an approximation formula.

Advantageous Effects of Invention

The present invention provides a method for nondestructively and readily inspecting whether or not a minute uneven structure whose two-dimensional size is less than 1 µm, such as a surface of a moth-eye mold, is within a predetermined range.

DESCRIPTION OF EMBODIMENTS

Hereinafter, a mold inspection method of an embodiment of the present invention is described with reference to the drawings. In the description below, a method for inspecting a moth-eye mold which has a porous alumina layer for production of an antireflection film is exemplified, but the present invention is not limited to this example. The present invention is also applicable to inspection of a surface of the porous alumina layer which has a minute uneven structure whose two-dimensional size viewed in a direction normal to the surface ($D_p$) is less than 1 μm.

Firstly, the structure of a porous alumina layer that is a subject of the inspection method of the embodiment of the present invention is described with reference to FIG. 1 and FIG. 2.

Figure 1:
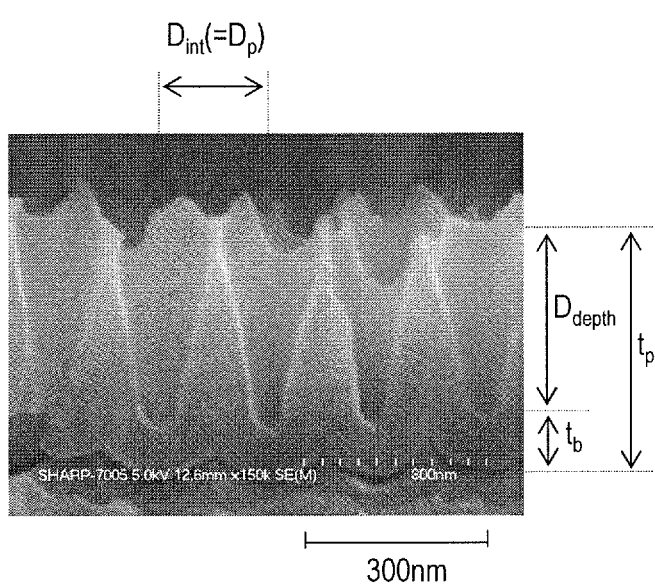
FIG. 1 A cross-sectional SEM image of a porous alumina layer which is used in production of an antireflection film.

FIG. 1 is a cross-sectional SEM image of the porous alumina layer that is used in production of an antireflection film. Further, a schematic structure of this porous alumina layer 6 is shown in FIGS. 2(a) and 2(b).

Figure 2:
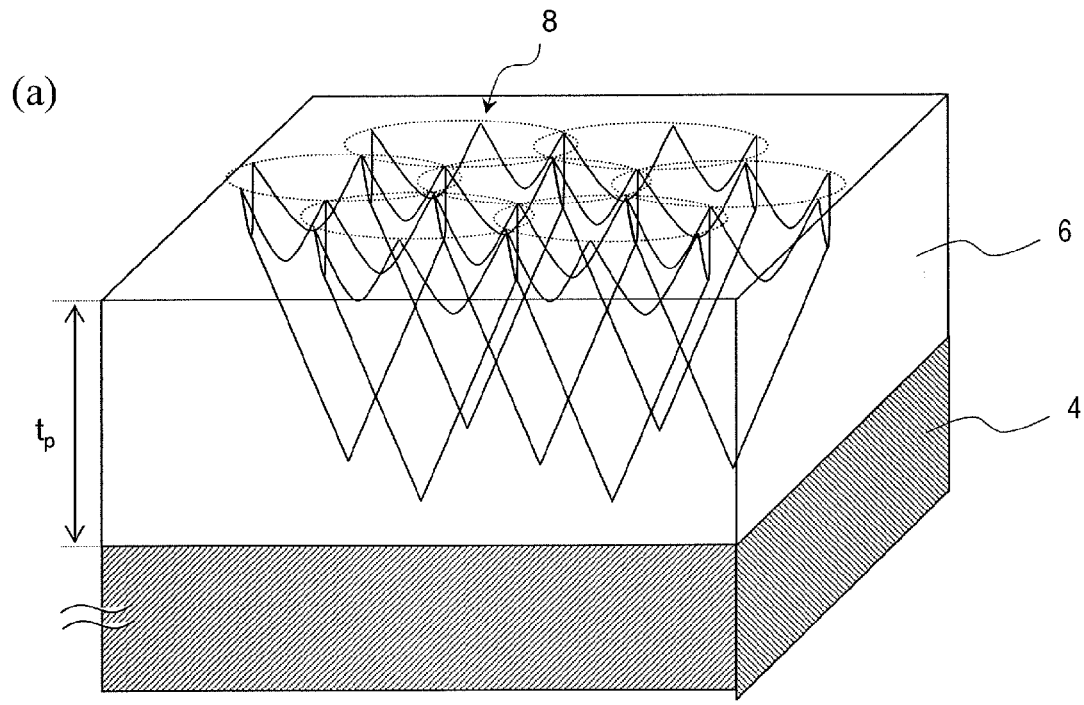
FIGS. 2 (*a*) and (*b*) schematically show a structure of a porous alumina layer which is used in production of an antireflection film.
Figure 2:
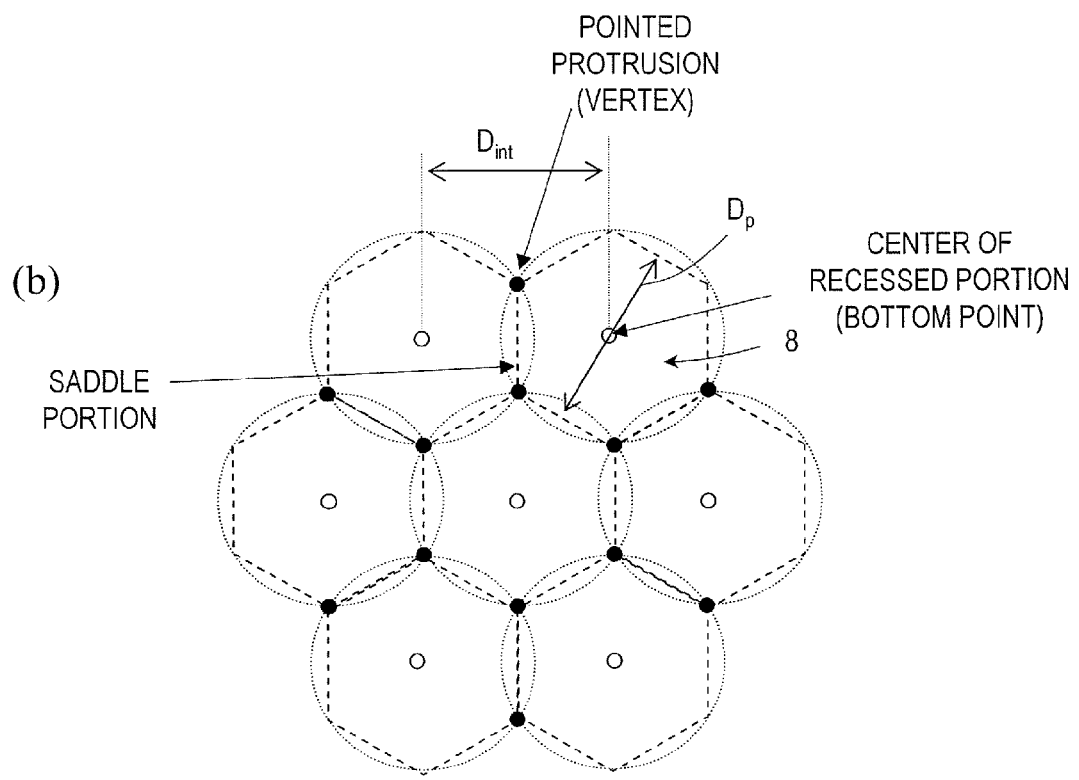
Figure 3:
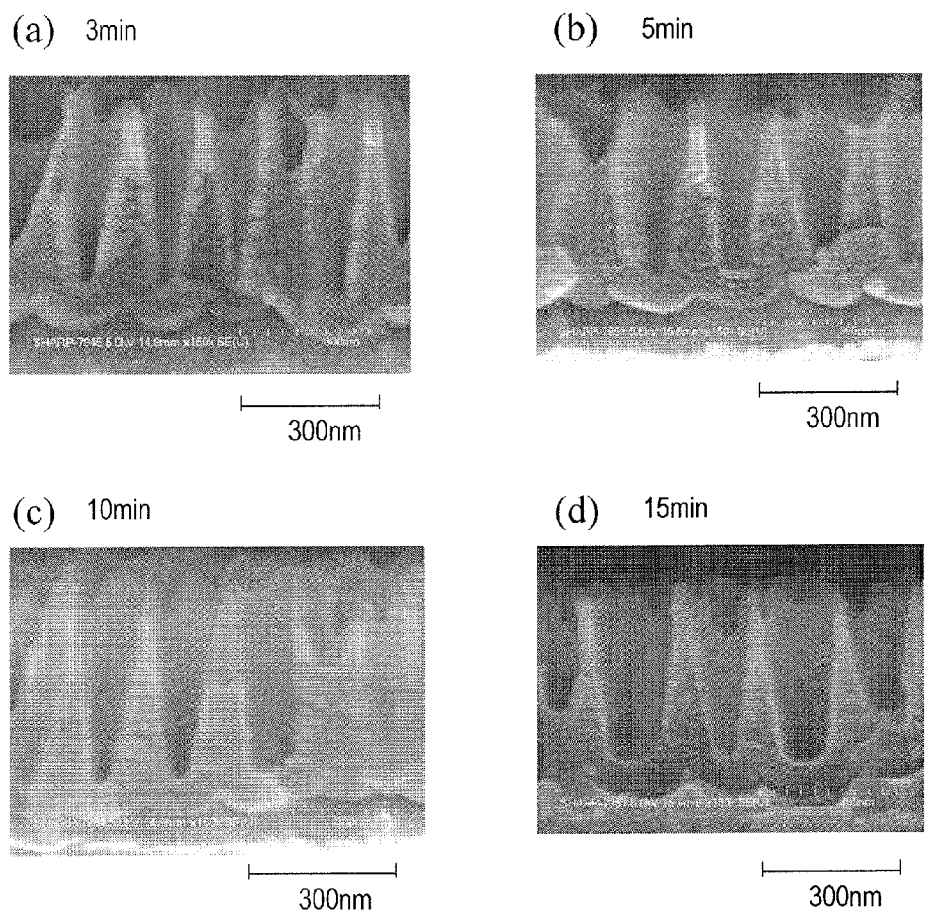
FIG. 3 (*a*) to (*d*) are cross-sectional SEM images of a porous alumina layer.

As seen from FIG. 1 and FIG. 2, the porous alumina layer 6 has a large number of minute recessed portions 8. The porous alumina layer 6 is obtained by performing anodization and etching on a surface of an aluminum base (or aluminum film) 4 as will be described later.

The cross-sectional shape of the minute recessed portions of the porous alumina layer that is used in production of an antireflection film is generally conical. It is preferred that the two-dimensional size of the minute recessed portions 8 (opening diameter: $D_p$) is not less than nm and less than 500 nm, and the depth of the minute recessed portions 8 ($D_{depth}$) is generally not less than 10 nm and less than 1000 nm (1 μm). It is also preferred that the bottom portion of the minute recessed portions 8 is tapered (with the deepest part of the bottom portion being pointed). Further, it is preferred that the minute recessed portions 8 are in a closely packed arrangement. Assuming that the shape of the minute recessed portions 8 of the porous alumina layer 6 when viewed in a direction normal to the porous alumina layer 6 is a circle, it is preferred that, as shown in FIG. 2, adjacent circles overlap each other, and a saddle portion is formed between adjacent ones of the minute recessed portions 8. Note that, when the generally-conical minute recessed portions 8 adjoin one another so as to form saddle portions, the two-dimensional size of the minute recessed portions 8, $D_p$, is equal to the average adjoining distance $D_{int}$. Thus, the porous alumina layer 6 of the moth-eye mold that is for formation of the antireflection film preferably has a configuration in which the minute recessed portions 8 are in an irregular closely-packed arrangement, the minute recessed portions 8 having such dimensions that $D_p = D_{int}$ is not less than 10 nm and less than 500 nm and $D_{depth}$ is generally not less than 10 nm and less than 1000 nm (1 μm). Strictly speaking, the shape of the openings of the minute recessed portions 8 is not a circle. $D_p$ is preferably determined from the SEM image of the surface. The thickness of the porous alumina layer 6, $t_p$, is generally not more than 1 μm.

The porous alumina layer whose cross-sectional SEM image is shown in FIG. 1 satisfies the above conditions. Specifically, $D_{int} = D_p = 180$ nm, $D_{depth} = 300$ nm, and $t_p = 400$ nm. The thickness of a barrier layer, $t_b$, is about 100 nm. This porous alumina layer was formed as described below.

Firstly, an aluminum film (about 1 μm thick) deposited on a glass substrate was anodized with a forming voltage of 80 V for 60 seconds using a 0.1 M oxalic acid aqueous solution (18° C.) as the electrolytic solution and thereafter immersed in a 2 mass % phosphoric acid aqueous solution (30° C.) as the etching solution for 90 minutes, whereby an anodized layer formed in the previous anodization step was removed. The minute uneven structure of the first-formed porous alumina layer is unstable in many cases, and therefore, it is preferred, for improvement of reproducibility, that the first-formed porous alumina layer is removed, and thereafter, another porous alumina layer is formed.

Thereafter, the anodization step (5 cycles) and the etching step (4 cycles) were alternately repeated using the aforementioned electrolytic solution (at the same temperature) and the aforementioned etching solution (at the same temperature). Thus, the process was finished with the anodization step. The duration of one cycle of the anodization step was 25 seconds, and the duration of one cycle of the etching step was 19 minutes (these conditions were the same as those of Sample C which will be described below). As the anodization duration is increased, the depth of the minute recessed portions increases. As the etching duration is increased, the opening diameter of the minute recessed portions increases. The structure of the minute recessed portions can be controlled by alternately performing the anodization and the etching respectively for appropriate durations.

Here, the minute uneven structure at the surface of the porous alumina layer varies mainly due to a variation of the duration of the anodization step and a variation of the duration of the etching step, and as a result, defective products can be manufactured. Among others, a variation of the temperature of the electrolytic solution and a variation of the temperature of etching solution can affect the minute uneven structure. In either case, the minute uneven structure is attributed to a variation in degree of the anodization and a variation in degree of the etching.

In view of the above circumstances, seven samples A to G were prepared with varying anodization durations as shown in Table 1 below. In Table 1, the formation conditions of the porous alumina layer, the thickness of the obtained porous alumina layer, $t_p$, and the results of color evaluation by visual observation are shown together. Note that a porous alumina layer was once formed and then removed as described above before the anodization (AO) step and the etching (Et) step shown in Table 1. The forming voltage and the type and temperature of the electrolytic solution and the etching solution were the same as those mentioned above. The thickness of the porous alumina layer, $t_p$, was determined from a cross-sectional SEM image such as shown in FIG. 1. The color evaluation of the porous alumina layer by visual observation will be described later.

TABLE 1

| Sample Name | AO | Et | Thickness $t_p$ nm | Color evaluation by visual observation |
|---|---|---|---|---|
| A | 15 sec × 5 cycles | 19 min × 4 cycles | 231 | pale blue |
| B | 20 sec × 5 cycles | ↑ | 328 | pale yellow |
| C | 25 sec × 5 cycles | ↑ | 387 | orange |
| D | 30 sec × 5 cycles | ↑ | 469 | pale purple |
| E | 33 sec × 5 cycles | ↑ | 498 | purple |
| F | 35 sec × 5 cycles | ↑ | 520 | purple |
| G | 40 sec × 5 cycles | ↑ | 600 | yellowish green |

As seen from Table 1, as the anodization duration increases, the thickness of the porous alumina layer, $t_p$, increases. Here, although only the thickness of the porous alumina layer, $t_p$, is shown, the depth of the minute recessed portions, $D_{depth}$, increases according to the increase of the thickness of the porous alumina layer $t_p$. Thus, the thickness of the porous alumina layer, $t_p$, can be recognized as a parameter that is indicative of the depth of the minute recessed portions, $D_{depth}$. Particularly when the process of forming the porous alumina layer is finished with the anodization step as exemplified herein, the correlation between $t_p$ and $D_{depth}$ is high as compared with a case where the process is finished with the etching step. Among samples A to G, the duration of the anodization step is different, but the duration of the etching step is equal. The samples A to G can be recognized as having generally similar cross-sectional shapes of the minute recessed portions, while only the thickness of the porous alumina layer, $t_p$, and the depth of the minute recessed portions, $D_{depth}$, are different. As a matter of course, $D_{int}$ is generally equal among samples A to G. These details were ascertained from cross-sectional SEM images.

Then, a porous alumina layer was formed under the same conditions as those for aforementioned sample C, and thereafter, additional etching is performed to vary the etching duration, such that four samples J to M shown in Table 2 below were prepared.

TABLE 2

| Sample Name | Additional Et | Shape of minute recessed portions | Color evaluation by visual observation |
|---|---|---|---|
| J | 3 min | narrow | pale purple |
| K | 5 min | medium | pink |
| L | 10 min | slightly wide | orange |
| M | 15 min | wide | yellow |

As seen from Table 2, as the etching duration increases, the minute recessed portions become wider. Cross-sectional SEM images of samples J to M are shown in FIGS. 3(a) to 3(d). As seen from FIGS. 3(a) to 3(d), samples J to M can be recognized as having difference shapes of the minute recessed portions, while the thickness $t_p$ and the depth $D_{depth}$ of the porous alumina layer are generally equal ($t_p = D_{depth}$). As a matter of course, strictly speaking, the thickness $t_p$ of the porous alumina layer is greater than the depth $D_{depth}$ by the thickness $t_b$ of the barrier layer. $D_{int}$ is generally equal among samples J to M.

Figure 4:
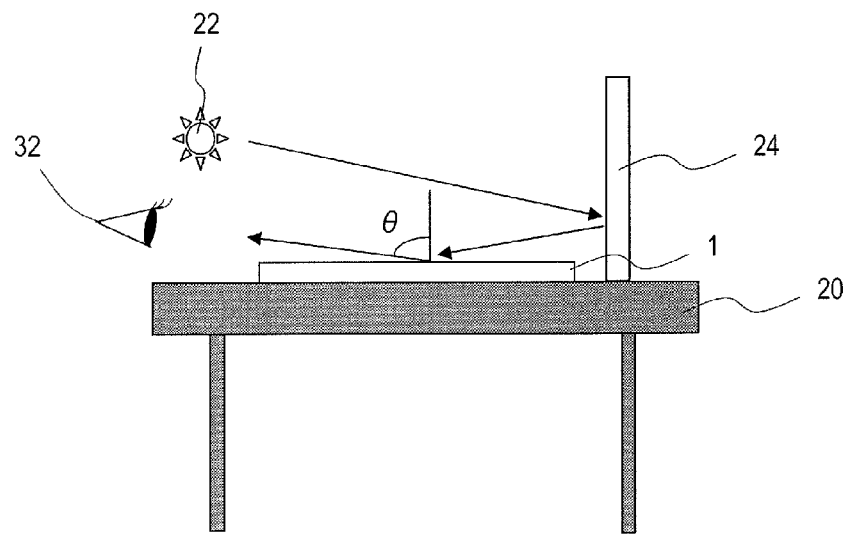
FIG. 4 A diagram for schematically showing how to evaluate the color of reflected light from a porous alumina layer by visual observation.

The porous alumina layers of samples A to G of Table 1 and samples J to M shown in Table 2 appear to have different colors. Specifically, reflected light appears tinted. The color of reflected light was evaluated as shown in FIG. 4. Specifically, a sample 1 with a porous alumina layer over its surface was placed generally horizontally on an examination table 20. Light emitted from a white light source (e.g., fluorescent lamp) 22 was reflected by a diffuse reflection plate 24 so as to strike the surface of the porous alumina layer, and reflection from the surface with reflection angle θ of approximately 90° was evaluated by an observer 32 by means of visual observation. The results of the evaluation are shown in Tables 1 and 2.

As seen from Tables 1 and 2, the color of the reflected light sensitively varies depending on thickness $t_p$ (depth $D_{depth}$) and the shape (width) of the recessed portions. Various samples were prepared according to the same method as that described above, and the relationship between thickness $t_p$ and the shape (width) of the recessed portions and the color of the reflected light was mapped in FIG. 5.

Figure 5:
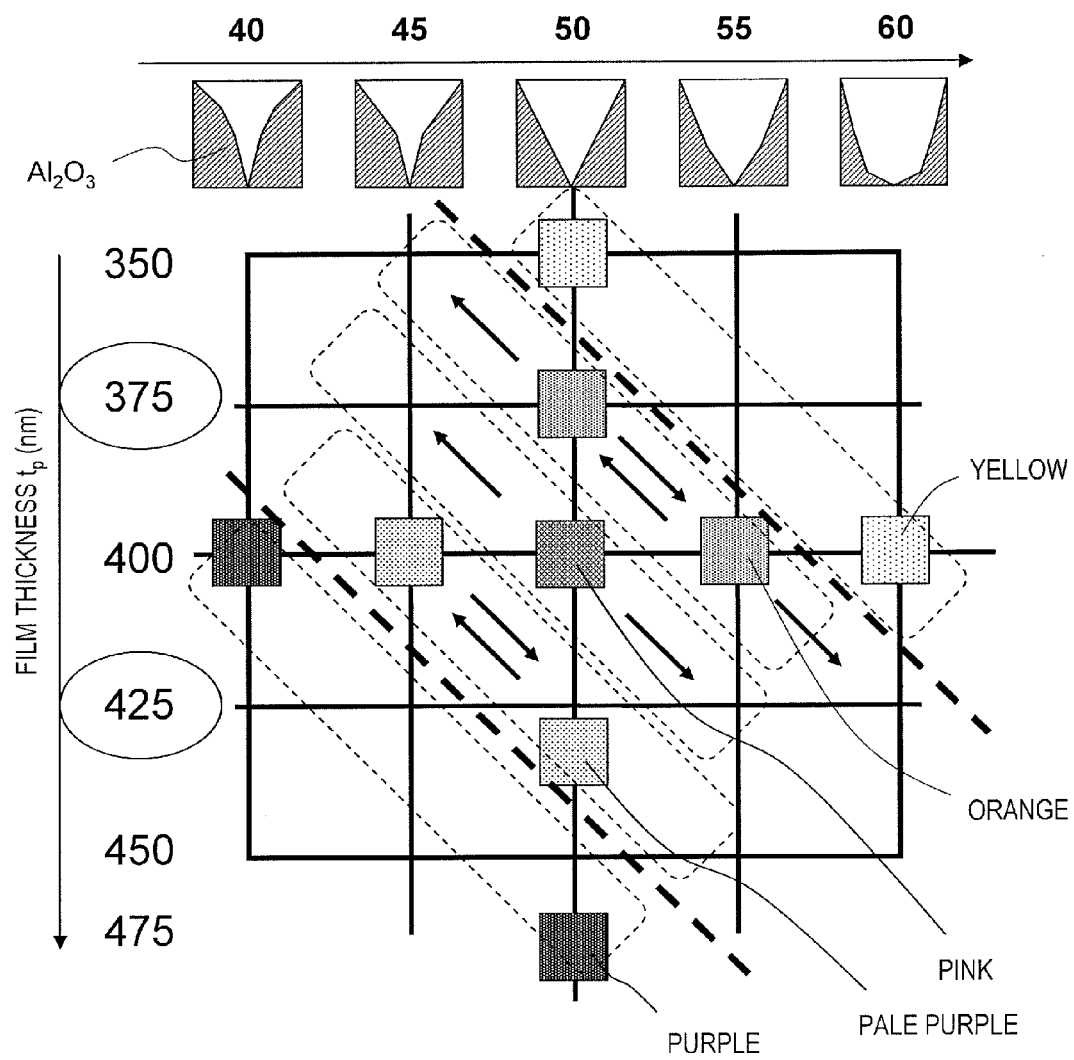
FIG. 5 A chart illustrating the relationship between the thickness of the porous alumina layer, $t_p$, and the shape of a recessed portion (recessed portion occupancy) and the color of reflected light.

Now, the recessed portion occupancy (%) is discussed, which serves as a parameter that quantitatively expresses the shape (width) of the recessed portions. As appreciated from the cross-sectional SEM images shown in FIG. 3, when the etching amount varies, the width of the recessed portions also varies. That is, the volume of the recessed portions varies. Since $D_{int}$ is determined proportionally to the forming voltage, $D_{int}$ is not dependent on the etching amount. Therefore, three-dimensionally, the minute uneven structure of the porous alumina layer can be approximately expressed as an assembly of cylindrical unit structures with a diameter of $D_p$ ($=D_{int}$). The cross section of this cylinder (including the diameter) has a rectangular shape as shown in FIG. 5. Specifically, the breadth of the rectangle is $D_p$ ($=D_{int}$), and the height of the rectangle is $D_{depth}$. As the width of the recessed portions increases, the area ratio of the recessed portions in the cross section of the rectangle also increases. In FIG. 5, the area ratio of the recessed portions to the area of the rectangle is represented as the occupancy of the recessed portions. Note that the occupancy of the recessed portions may be represented by the volume ratio of the recessed portions to the cylinder, instead of the area ratio of the recessed portions. As seen from the above example, the duration of one cycle of the etching step is long, e.g., from a few minutes to 20 minutes, whereas the duration of one cycle of the anodization step is several tens of seconds. It is therefore inferred that the variation of the shape (width) of the recessed portions which is caused by the etching step is small, and approximation of the recessed portion occupancy by the area ratio would not cause any problem.

FIG. 5 illustrates the relationship between thickness $t_p$ and the recessed portion occupancy and the color of reflected light, where a porous alumina layer which is configured such that thickness $t_p$ is 400 nm and the recessed portion occupancy is 50% is at the center. Thickness $t_p$ and the recessed portion occupancy were determined from the cross-sectional SEM images, and the color of reflected light was evaluated according to the method that has previously been described with reference to FIG. 4.

As seen from FIG. 5, the porous alumina layer that is present at the center (thickness $t_p$: 400 nm, recessed portion occupancy: 50%) appears pink. As thickness $t_p$ increases, the color changes to orange and then yellow. As thickness $t_p$ decreases, the color changes to pale purple and then purple. As the recessed portion occupancy increases, the color changes to orange and then yellow. As the recessed portion occupancy decreases, the color changes to pale purple and then purple. Thus, only checking the color would not help to determine whether thickness $t_p$ varies or the recessed portion occupancy varies. For example, for thicknesses $t_p$ of 375 nm, 400 nm, and 425 nm, the reflected light appears pink when the recessed portion occupancy is 45%, 50%, and 55%, respectively. Likewise, the values of thickness $t_p$ and the recessed portion occupancy are within the regions encircled by broken lines in FIG. 5, the reflected light appears in the same color.

In the case of forming a porous alumina layer which is configured such that thickness $t_p$ is 400 nm and the recessed portion occupancy is 50%, if thickness $t_p$ is 400 nm±40 nm (boundary lines represented by thick broken lines in FIG. 5) and the recessed portion occupancy (here, the area ratio) is not less than 45% and not more than 55%, a resultant product will be regarded as a good product. This criterion was determined based on the antireflection property of an antireflection film which was produced using a moth-eye mold that includes a porous alumina layer. This criterion for determination of a good product is merely an example. The reference values (thresholds) of thickness $t_p$ and the recessed portion occupancy are appropriately determined.

Next, a method for nondestructively and readily inspecting whether or not the minute uneven structure at the surface of the porous alumina layer is within a predetermined range, specifically, in the above example, whether or not thickness $t_p$ is 400 nm±40 nm and whether or not the recessed portion occupancy (here, the area ratio) is in the range of not less than 45% and not more than 55%, was examined. Here, 400 nm was the center value, but the center value is not limited to this value. For example, even when 200 nm is employed as the center value, the color varies within the range of ±40 nm, and there is no probability that the same color repeatedly occurs in this range (e.g., the same color occurs at +40 nm and −40 nm). The method that is exemplified herein is applicable without making any modification.

First, a method for nondestructively and readily inspecting whether or not the thickness of the porous alumina layer, $t_p$, is within a predetermined range (e.g., within the range of 400 nm±40 nm) was examined. As previously described, in the process of forming a porous alumina layer, the duration of one cycle of the etching step is long, e.g., from several minutes to about 20 minutes, whereas the duration of one cycle of the anodization step is several tens of seconds. Therefore, the variation of the shape (width) of the recessed portions which is caused in the etching step is small. A factor which actually matters in a mass-production process is management of the thickness of the porous alumina layer, $t_p$, (which is associated with the depth of the minute recessed portions).

A mold inspection method of an embodiment of the present invention includes the steps of: (a) providing, based on the relationship between the first parameter that is indicative of the thickness of a porous alumina layer and a color parameter that is indicative of the color of reflected light from the porous alumina layer, the first color information which represents a tolerance of the first parameter of the porous alumina layer which has an uneven structure that is within a tolerance; (b) providing a mold which is an inspection subject, the mold having a porous alumina layer over its surface; (c) obtaining a color parameter which is indicative of the color of reflected light from the porous alumina layer of the inspection subject mold; and (d) determining the suitability of the first parameter of the inspection subject mold based on the obtained color parameter and the first color information.

In step (a), the first color information is provided which represents the tolerance of the first parameter of the porous alumina layer that has an uneven structure that is within a tolerance based on the relationship between the first parameter and the color parameter which has been prepared beforehand. The first parameter may be the thickness of the porous alumina layer, $t_p$, which is correctly determined from a cross-sectional SEM image, for example, or the depth of the recessed portions, $D_{depth}$, which is directly associated with thickness $t_p$. The color parameter represents the color of reflected light from the porous alumina layer. The color parameter is, for example, tristimulus values (X, Y and Z).

Here, the porous alumina layer that has an uneven structure that is within a tolerance refers to a porous alumina layer in which a parameter other than the first parameter (here, the shape (width) of the recessed portions which is represented by the recessed portion occupancy) is within a tolerance. For example, it includes porous alumina layers which are represented by five boxes aligned along the vertical line of the 50% recessed portion occupancy in FIG. 5. The first color information which represents the tolerance of the first parameter of these porous alumina layers refers to, in the example shown in FIG. 5, color information which represents that thickness $t_p$ is not less than 375 nm and not more than 425 nm. As previously described, when the inspection is realized by visual observation, the information that "the color of reflected light is any of orange, pink, and pale purple, or any color between these colors" corresponds to this first color information. The first color information is computer-processable information and is determined based on the above-described color parameter. For example, it may be the lower limit value and the upper limit value which are represented by tristimulus values (X, Y and Z) (also referred to as "thresholds" or "boundary values").

Then, the color parameter is obtained in step (c) which represents the color of reflected light from the porous alumina layer of the inspection subject mold prepared in step (b). This color parameter is to be compared with the first color information and is equivalent to the color parameter in step (a). The color parameter is, for example, tristimulus values.

Lastly, in step (d), the color parameter obtained in step (c) and the first color information which is represented by the color parameter are compared in order to determine whether or not the first parameter of the inspection subject mold is within the tolerance.

The condition that it can be determined using the color parameter whether or not the first parameter that is indicative of thickness $t_p$ is within a desired range means that the thickness of the porous alumina layer, $t_p$, can be indirectly measured using the color parameter. Determining thickness $t_p$ with the use of the color parameter provides various advantages as described below.

A commonly-known method for measuring the thickness of a thin film is a measuring method in which an ellipsometer is used. Using an ellipsometer enables to accurately determine the thickness of a single layer film whose complex refractive index is known. The porous alumina layer includes a layer which is constituted of the minute recessed portions and a barrier layer. The complex refractive index of the porous layer is not constant but varies along the thickness direction according to the proportion of alumina portions and vacancy portions. Further, the bottom of the barrier layer is not flat, and therefore, there is a layer in which alumina and an aluminum layer are intermingled with each other. To determine the thickness of a porous alumina layer which has such a complex layer structure using an ellipsometer, appropriate modeling of the complex layer structure is necessary. Thus, the determined thickness varies depending on the accuracy of the model, so that sufficient accuracy cannot be obtained. To realize a measurement using an ellipsometer, it is necessary to adjust two optical axes, the optical axis on the light emission side and the optical axis on the light detection side, so that the measurement is difficult. Particularly in a mass-production line, it is difficult to evaluate the uneven structure of a large-surface porous alumina layer at a plurality of positions, and an apparatus would be expensive. Thus, this is not a realistic case.

On the other hand, the color parameter can be determined from the spectral reflectance, for example. Measurement of the spectral reflectance (reflection spectrum) only requires setting of the optical axis on the light receiving side, and the accuracy in setting of the optical axis may not be high. For example, a spectral color measuring system COMES (registered trademark) manufactured by NIRECO CORPORATION enables to determine tristimulus values X, Y and Z from the spectral reflectance. The color parameter is not limited to the tristimulus values but may be L*, a*, b*, for example.

Figure 6:
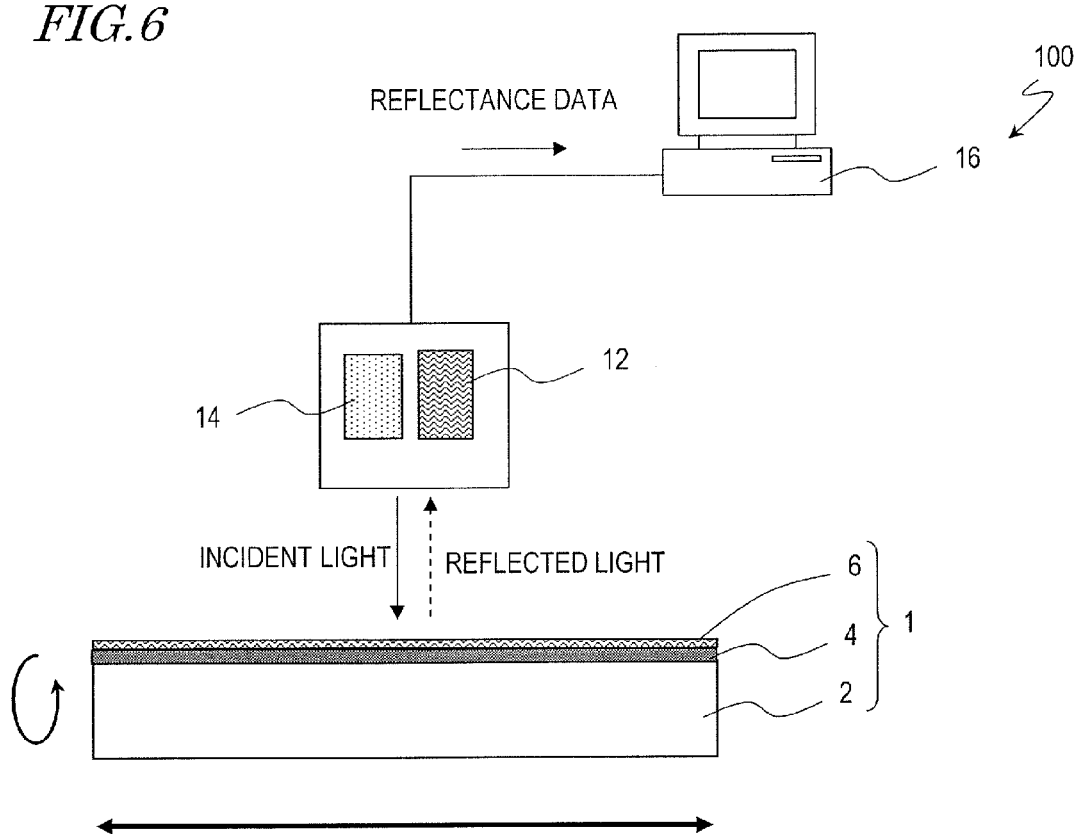
FIG. 6 A schematic diagram showing a configuration of an inspection system 100 which is used for a mold inspection method of an embodiment of the present invention.

The mold inspection method of an embodiment of the present invention may be realized by using an inspection system 100 shown in FIG. 6. The inspection system 100 shown in FIG. 6 includes a white light source 12, a spectroscope 14, and a computer 16 which is configured to control the white light source 12 and the spectroscope 14 and to process data obtained from the spectroscope 14. The computer 16 includes an operational processing unit and a memory unit. The memory unit stores data obtained from the spectroscope 14 and data of the first color information, and the like, as well as software for various operational processing.

The inspection system 100 quantitatively determines the color of reflected light from the porous alumina layer as follows. As shown in FIG. 6, the white light source 12 and the spectroscope 14 of the inspection system 100 are placed at predetermined positions relative to an inspection subject mold 1. The inspection subject mold 1 includes, for example, a support 2, an aluminum film 8 deposited on the support 2, and a porous alumina layer 6 which is formed by anodizing a surface of the aluminum film. Light is emitted from a white light source 12 (e.g., white LED, a xenon lamp) of the inspection system 100 toward the surface of the porous alumina layer 6 of the mold 1. Of the light incident on the porous alumina layer 6, reflected light strikes the spectroscope 14, and the reflectances for respective wavelengths are determined. The measured wavelength range is, for example, from 400 nm to 700 nm. The wavelength resolution is 1.5 nm. The measurement duration is 155 msec at each point.

Figure 7:
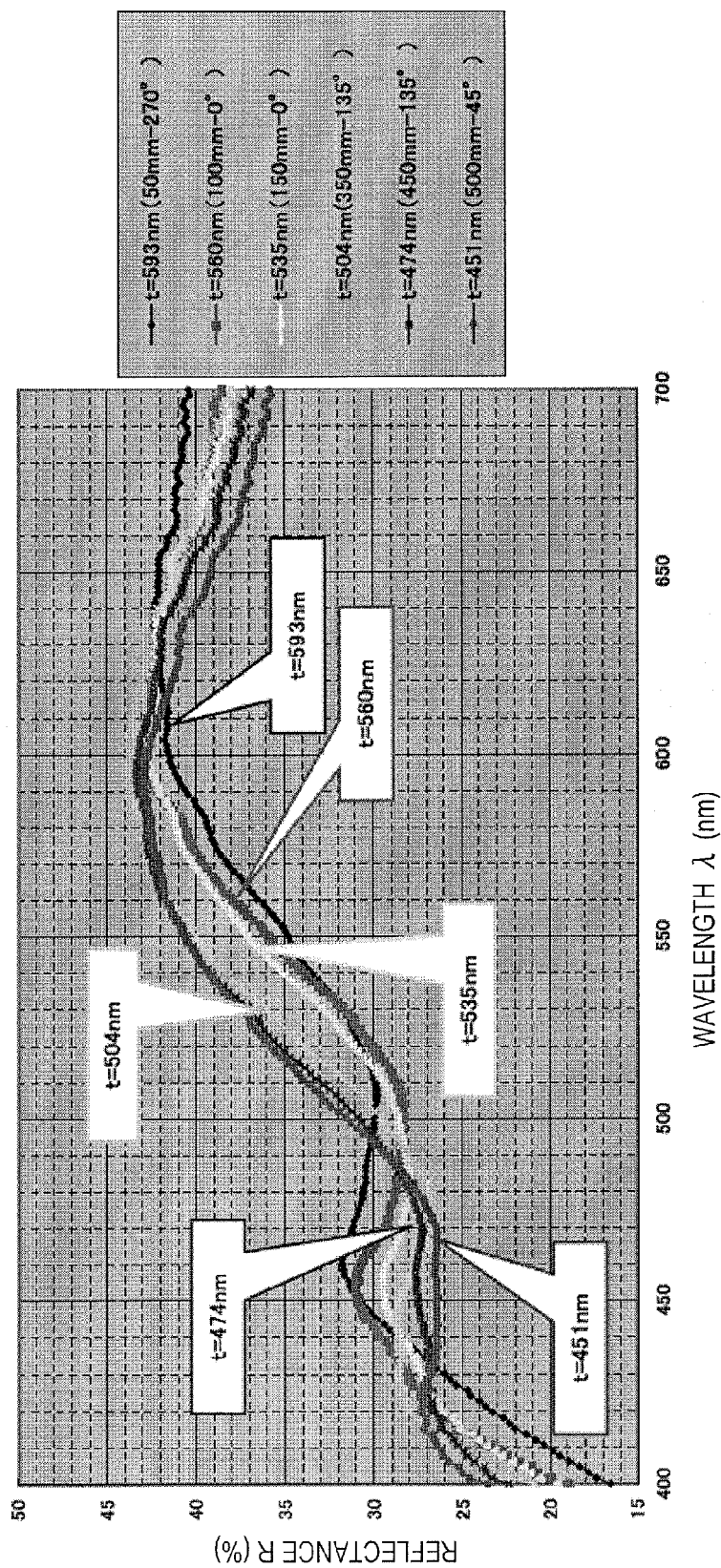
FIG. 7 A graph showing examples of the spectral reflectance characteristic (reflection spectrum) of a porous alumina layer.

For example, a spectral reflectance characteristic (reflection spectrum) such as shown in FIG. 7 is obtained. Here, the vertical reflectance (Rv) was measured. The reflection spectrum illustrated herein is a measurement result for a porous alumina layer which was formed over a surface of a cylindrical aluminum base (diameter: 150 mm, length: 600 mm) such that the thickness of the porous alumina layer, $t_p$, is 520 nm as in previously-described sample F. In FIG. 7, 50 mm-270° of "t=593 nm (50 mm-270°)" represents a measuring position at the porous alumina layer formed on the surface of the cylinder. 50 mm is the length measured from the upper end of the cylinder (e.g., the upper end of the cylinder when immersed in a treatment solution in the anodization and the etching). 270° is the angle for specifying the coordinates over the perimeter of the cylinder, which refers to the angle that is formed by a line extending between the measuring point and the center of the cylinder with a reference line (a line extending between the reference point and the center of the cylinder). The reference point may be any point and may be appropriately determined according to the setting of the apparatus. The spectral reflectance characteristic is stored together with the information about the measuring point in the computer 16.

The wavelength represented by t=593 nm is a wavelength for which the reflectance has an extreme value (local maximum or local minimum). From the extreme value, the film thickness can be estimated according to a peak-valley method (PV method). Note that, however, to determine a wavelength for which the reflectance has an extreme value, it is necessary to correct the reflectance. The wavelengths shown in FIG. 7 are wavelengths for which the corrected reflectance has an extreme value. To determine the film thickness of the porous alumina layer according to the PV method, it is necessary to determine the refractive index of the porous alumina layer according to an appropriate model as in the case of using an ellipsometer.

The operation of determining the tristimulus values from the spectral reflectance characteristic is carried out by the computer 16. The result of the operation is stored in the memory unit and, meanwhile, when necessary, output to a display, printer, or the like. The operation of determining the color parameter, such as the tristimulus values, from the spectral characteristics and the operation for conversion between color parameters are well known, and therefore, the descriptions thereof are omitted herein.

The first color information that serves as a criterion for determination of good products may be determined, for example, as described below. In the example described hereinafter, film thickness $t_p$ is the target of management.

Figure 8:
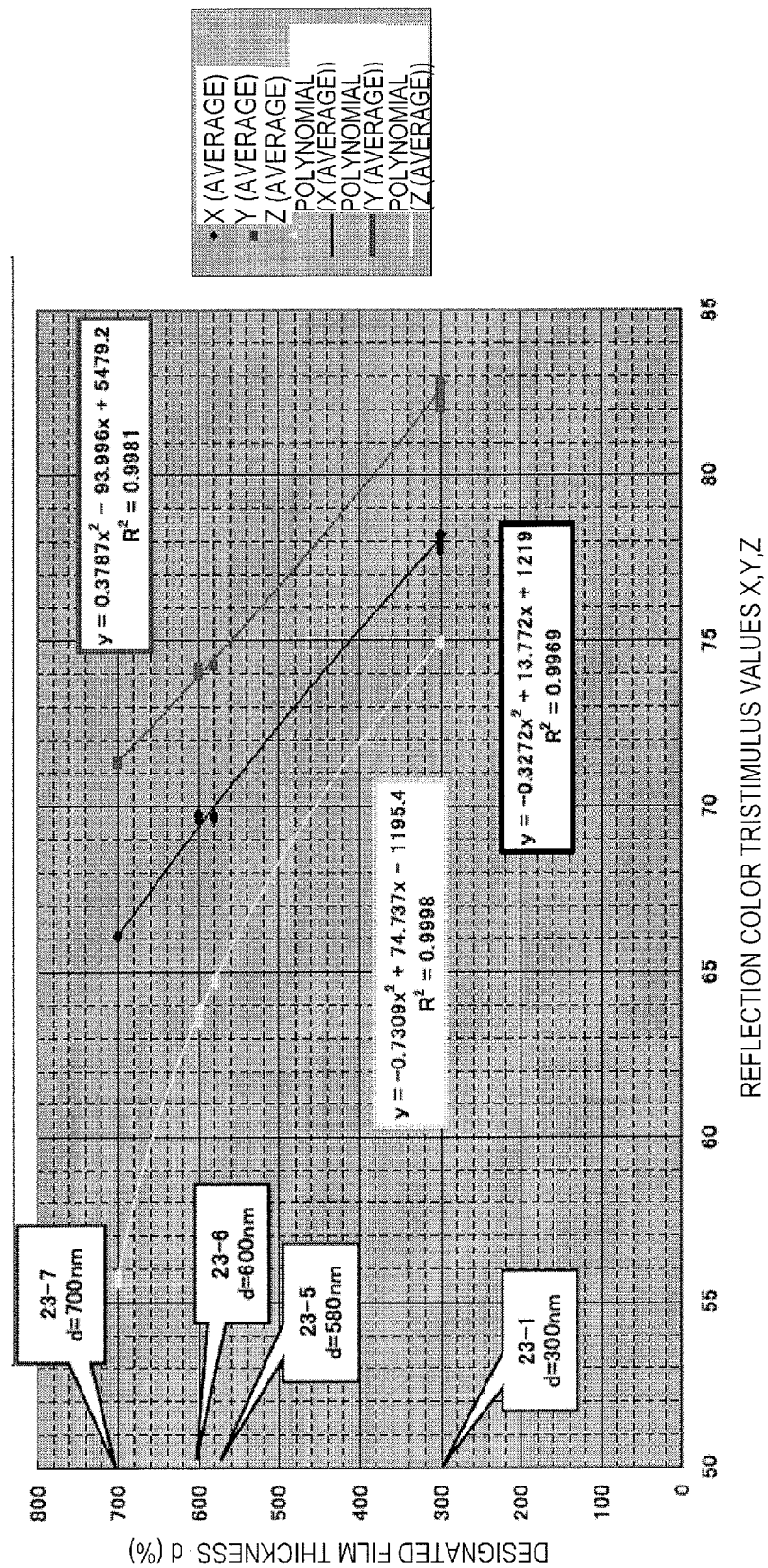
FIG. 8 A graph showing the correlation between the thickness of the porous alumina layer, $t_p$, and each of the tristimulus values X, Y and Z.

Based on film thickness $t_p$ determined from a SEM image, a good product sample of which film thickness $t_p$ is within the tolerance, a film thickness lower limit sample of which film thickness $t_p$ is just below the lower limit of the tolerance, and a film thickness upper limit sample of which film thickness $t_p$ is just above the upper limit of the tolerance are prepared. For each of the samples, X, Y and Z are determined according to the above-described method. Each of the samples used herein satisfies a condition that the shape of the minute recessed portions (the recessed portion occupancy) is within a tolerance. The correlation function between film thickness $t_p$ and each of X, Y and Z is determined. For example, a relationship which is approximated by a curved line or a straight line such as shown in FIG. 8 is determined. As seen from FIG. 8, the correlation function between film thickness $t_p$ and each of X, Y and Z can typically be approximated by a quadratic polynomial. For each sample, X, Y and Z and the quadratic polynomials thereof are stored in the memory unit of the computer 16. The first color information includes the values of Xa, Ya, and Za of the film thickness lower limit sample and the values of Xb, Yb, and Zb of the film thickness upper limit sample.

As seen from FIG. 8, X and Y are generally proportional to film thickness $t_p$ and are therefore associated with film thickness $t_p$ at higher accuracy than in the case where Z is used. Thus, using X and/or Y as the color parameter is preferred. It is not necessary to determine every one of the relationships between X, Y and Z and film thickness $t_p$.

For the porous alumina layer of the inspection subject mold, X, Y and Z are determined according to the above-described method and compared with the first color information. Specifically, the determined X, Y and Z are compared with Xa, Ya, Za, Xb, Yb, and Zb to determine whether or not they lie between these values. If they lie within the range of these values, it is determined to be suitable. If they lie outside the range, it is determined to be not suitable. Further, thickness $t_p$ can be determined by substituting corresponding X, Y or Z in the quadratic polynomial. As a matter of course, the suitability may be determined based on $t_p$.

When inspecting a large-surface porous alumina layer, X, Y and Z are obtained from each of a plurality of different positions over the surface of the porous alumina layer, and X, Y and Z obtained from each of the plurality of positions are compared with Xa, Ya, Za, Xb, Yb, and Zb to determine whether or not they lie between these values. Here, the mold 1 may be moved relative to the white light source 12 and the spectroscope 14 as illustrated by a two-way arrow in FIG. 6. When a roll mold which has a porous alumina layer over the surface of a cylindrical aluminum base is used instead of the mold 1, it is preferred to obtain X, Y and Z from each of the plurality of positions while rotating the roll mold around its central axis. When the color parameter is obtained from a plurality of positions over the porous alumina layer in this way, it is preferred to store the color parameter in association with each measuring position.

In general, the uneven structure of a large-surface porous alumina layer has non-uniformity. Typically, the recessed portions are deeper (thickness $t_p$ is greater) at a position which is closer to the edge of the mold. This is because the anodization advances more readily at a position which is closer to the edge. Based on such a predetermined relationship between the positions over the surface of the porous alumina layer and the first parameter, the suitability of the first parameter may be determined. For example, the measurement results at two different positions are compared. If they satisfy the above-described relationship, it is determined to be suitable. If they do not satisfy the above-described relationship, it is determined to be not suitable. In the case where there are a large number of measuring points over a large-surface porous alumina layer, the general tendency of the distribution of the largeness of the value of X, Y or Z is converted into a numerical expression for determination of the suitability.

When the measurement result does not accord with the predetermined relationship between positions over the surface of the porous alumina layer and the first parameter, there is a probability that the shape of the minute recessed portions (recessed portion occupancy) is outside the tolerance.

In that case, the suitability of the occupancy of the recessed portions (second parameter) may be determined as in the above-described method that is for determining the suitability of the film thickness (first parameter).

Specifically, the step of providing the second color information which represents the tolerance of the second parameter of the porous alumina layer which has the uneven structure that is within the tolerance based on the relationship between the second parameter that represents the occupancy of a plurality of minute recessed portions of the porous alumina layer and the color parameter that represents the color of reflected light from the porous alumina layer and the step of determining the validity of the second parameter of the inspection subject mold based on the obtained color parameter and the second color information are further performed. The step of providing the second color information includes, as in the above-described method, providing a good product sample of which the recessed portion occupancy is within the tolerance, a recessed portion occupancy lower limit sample of which the recessed portion occupancy is just below the lower limit of the tolerance, and a recessed portion occupancy upper limit sample of which the recessed portion occupancy is just above the upper limit of the tolerance, and determining X, Y and Z for each of the provided samples according to the above-described method. Each of the samples used herein satisfies a condition that film thickness $t_p$ is within the tolerance. The correlation function between the recessed portion occupancy and each of X, Y and Z is determined. The correlation is expressed as an approximation formula in the same way as described above.

In the uneven structure of the porous alumina layer which is illustrated herein, the depth of the recessed portions (thickness $t_p$) is more likely to vary than the shape of the recessed portions (recessed portion occupancy). Therefore, in the inspection method previously exemplified, the first parameter that is indicative of thickness $t_p$ is first determined, and determination of the second parameter that is indicative of the shape of the recessed portions is optional. However, the present invention is not limited to this example. The reverse order may be employed.

Figure 9:
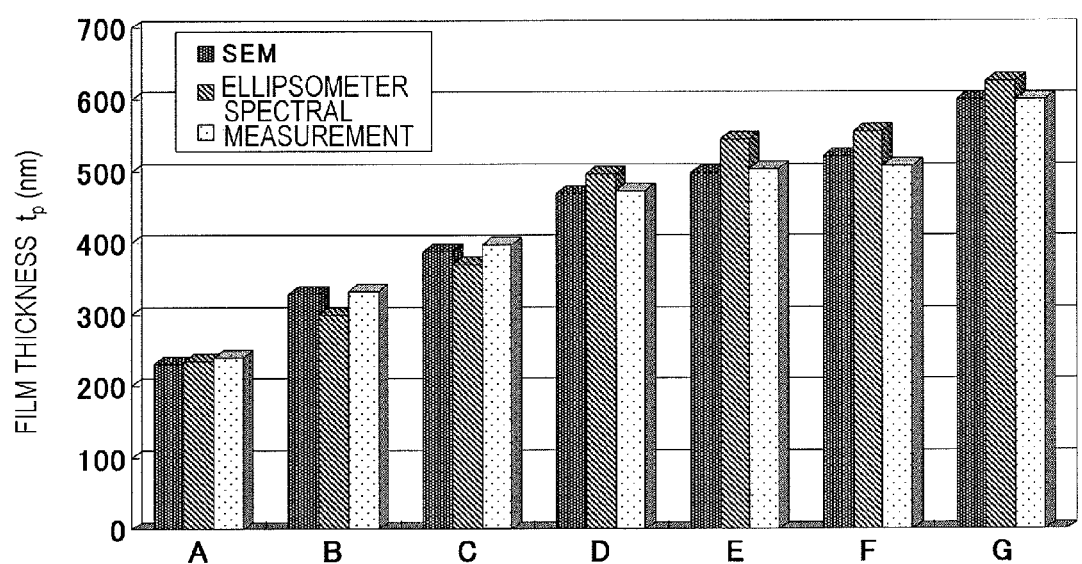
FIG. 9 A graph showing the measurement results of the film thickness of various porous alumina layers (samples A to G shown in Table 1).

FIG. 9 shows the results of indirect measurement of film thickness $t_p$ of samples A to G that have previously been illustrated in Table 1 based on the spectral reflectance ("spectral measurement" in FIG. 9). Here, samples A, B, F and G are reference samples, and quadratic polynomials are determined from the values of film thickness $t_p$ and X and Y which are determined from SEM images of these samples. For the shown results of samples C, D, and E, film thickness $t_p$ was determined by substituting the values of X and Y in the above quadratic polynomials. FIG. 9 shows together a film thickness which was determined from a SEM image and a film thickness which was determined using an ellipsometer. The ellipsometer used was a spectral ellipsometry (M-200, rotating compensator type) manufactured by J. A. Woollanm Co. Inc. The analysis model was such that the volume ratio of alumina portions and vacancy portions in the porous layer was 50:50, and the boundary region between the barrier layer and the aluminum layer was a 30 nm thick layer.

As clearly seen from FIG. 9, the thicknesses of samples C, D, and E which are determined by spectroscopy accord very well with the thicknesses determined from the SEM images. Note that the reason why they do not exactly accord is that only a local thickness is determined from a SEM image, whereas the spectroscopy provides the average value across a certain extent of area. On the other hand, the film thickness which is determined using an ellipsometer has a large variation. It is sometimes larger, and at other times smaller, than the thickness which is determined from a SEM image. Thus, the measurement accuracy is poor.

Thus, employing an inspection method of an embodiment of the present invention enables to nondestructively and readily inspect whether or not a minute uneven structure at the surface of a porous alumina layer is within a predetermined range.

Employing an inspection method of an embodiment of the present invention enables stable mass-production of a moth-eye mold that includes a porous alumina layer which is for production of an antireflection film. For example, an antireflection film can be produced as described below.

The surface of the porous alumina layer of a mold that is manufactured as described above is provided with a mold release treatment. On the other hand, a polymer film (e.g., TAC film) is provided as a base material for production of an antireflection film, and a photocurable resin (typically, acrylic UV-curable resin) is applied onto the polymer film. The uneven surface of the porous alumina layer which has been provided with a mold release treatment is pressed against the photocurable resin in vacuum. The photocurable resin that fills the uneven structure of the porous alumina layer is irradiated with ultraviolet light such that the photocurable resin is cured. The moth-eye mold is released from the polymer film, so that a cured material layer of the photocurable resin (antireflection film), to which the uneven structure of the moth-eye mold has been transferred, is obtained over the surface of the polymer film. When a cylindrical moth-eye mold is used as described above, an antireflection film can be continuously formed over the surface of a polymer film that is in the form of a roll according to a roll-to-roll method. The reflectance of the thus-formed antireflection film is, for example, not more than 0.2% at 550 nm. As a matter of course, an antireflection film whose reflectance is not more than 0.2% over the entire visible light wavelength range (A=380 nm to 780 nm) can also be obtained.

INDUSTRIAL APPLICABILITY

The present invention is suitably used for, for example, inspection of a moth-eye mold that includes a porous alumina layer which is for production of an antireflection film. The present invention is used for inspection of a porous alumina layer which is employed in other uses, for example, inspection of a porous alumina layer which has regularly-arranged cylindrical recessed portions.

REFERENCE SIGNS LIST

1 mold
2 support
4 aluminum film
6 porous alumina layer
12 white light source
14 spectroscope
16 computer
100 inspection system

The invention claimed is:

1. A method for inspecting a mold, the method comprising:
   (a) providing, based on a relationship between first parameter values indicative of respective thicknesses of porous alumina layers and color parameters indicative of respective colors of reflected light from respective porous alumina layers, first color information which respectively represent a range of the first parameter values for a respective color parameter;
   (b) providing the mold as an inspection subject, the mold including a porous alumina layer over its surface;
   (c) obtaining a color parameter indicative of a color of reflected light from the porous alumina layer of the inspection subject mold; and
   (d) determining a suitable range of first parameter values of the inspection subject mold based on the obtained color parameter and the provided first color information.

2. The method of claim 1, wherein the color parameter includes X or Y of tristimulus values X, Y and Z.

3. The method of claim 2, wherein step (a) includes expressing the relationship of the first parameter and X or Y as an approximation formula.

4. The method of claim 1, wherein step (c) includes measuring a spectral reflectance of the porous alumina layer of the inspection subject mold.

5. The method of claim 1, wherein
   step (c) includes obtaining the color parameter from each of a plurality of different positions over a surface of the porous alumina layer, and
   step (d) includes determining a suitable range of first parameter values of the inspection subject mold based on the color parameter obtained from each of the plurality of different positions and the provided first color information.

6. The method of claim 5, further comprising:
   (e) determining a suitable range of the first parameter values of the inspection subject mold based on a relationship between a position over a surface of the porous alumina layer and the first parameter value.

7. The method of claim 1, further comprising:
   (f) providing, based on a relationship between second parameter values each respectively indicative of an occupancy of a plurality of minute recessed portions of a respective porous alumina layer and a color parameters indicative of respective colors of reflected light from respective porous alumina layers, second color information which respectively represents a range of the second parameter values for a respective color parameter; and
   (g) determining a valid range of the second parameter values of the inspection subject mold based on the obtained color parameter and the provided second color information.

* * * * *